United States Patent [19]

Pearson

[11] Patent Number: 4,884,756
[45] Date of Patent: Dec. 5, 1989

[54] WASTE TREATMENT SYSTEM

[76] Inventor: Erich H. Pearson, 925 Oakwood Ct., Glen Ellyn, Ill. 60137

[21] Appl. No.: 305,473

[22] Filed: Feb. 1, 1989

[51] Int. Cl.$^4$ .............................................. B02C 23/38
[52] U.S. Cl. ...................................... 241/42; 241/60; 241/99; 241/100; 241/101 B
[58] Field of Search ................................ 366/297–301; 241/101 B, 99, 100, 236, DIG. 38, 159, 186 A, 60, 41, 42

[56] References Cited

U.S. PATENT DOCUMENTS

| | | | |
|---|---|---|---|
| 1,825,261 | 9/1931 | Burns et al. | 241/101 B X |
| 2,492,421 | 12/1949 | Golben | 241/101 B |
| 3,332,629 | 7/1967 | Miller . | |
| 3,901,349 | 8/1975 | DeNoyer . | |
| 3,926,379 | 12/1975 | Dryden et al. . | |
| 4,265,407 | 5/1981 | Kessler et al. | 241/101 B X |
| 4,344,579 | 8/1982 | Morita et al. | 241/101 B X |
| 4,362,628 | 12/1982 | Kennedy et al. . | |
| 4,618,103 | 10/1986 | Wilson et al. . | |
| 4,619,409 | 10/1986 | Harper et al. . | |

FOREIGN PATENT DOCUMENTS 619810 10/1935 Fed. Rep. of Germany .
1140899 6/1986 Japan ............................... 241/101 B Primary Examiner—Mark Rosenbaum
Attorney, Agent, or Firm—McAndrews, Held & Malloy, Ltd.

[57] ABSTRACT

A system for the treatment of infectious waste including apparatus for receiving, shredding, disinfecting, and separating waste material. A manually operated entry device provides input for quantities of solid waste into a feeding channel wherein a feeding ram moves the waste onto a series of shredding disintegrators which achieve material size reduction. Following shredding, the waste is gravitationally transferred into disinfecting fluid contained within an enclosed decontamination and separation device. Solid waste is continuously separated from the disinfecting fluid. The decontaminated solid waste is then deposited into a storage device.

11 Claims, 3 Drawing Sheets

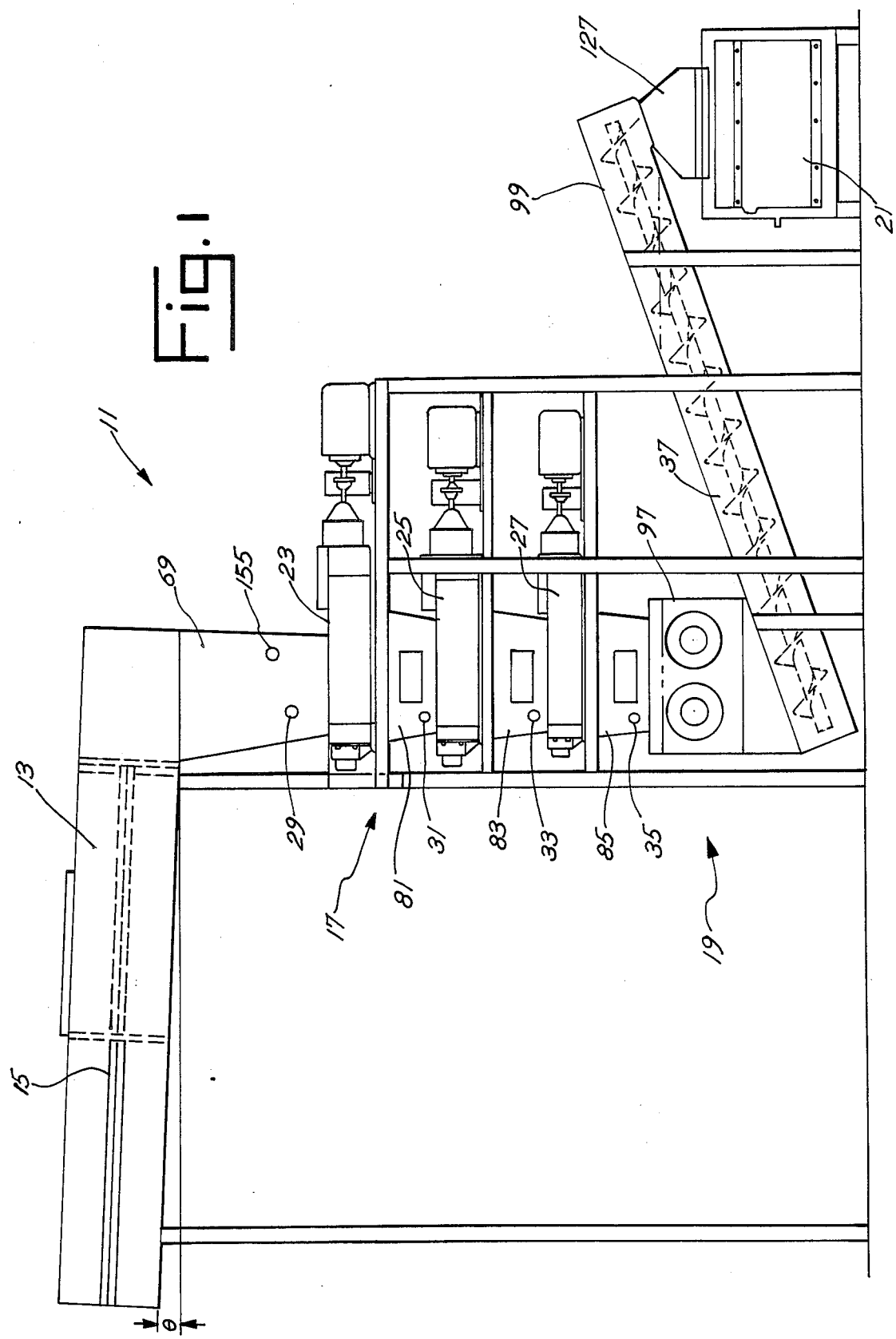

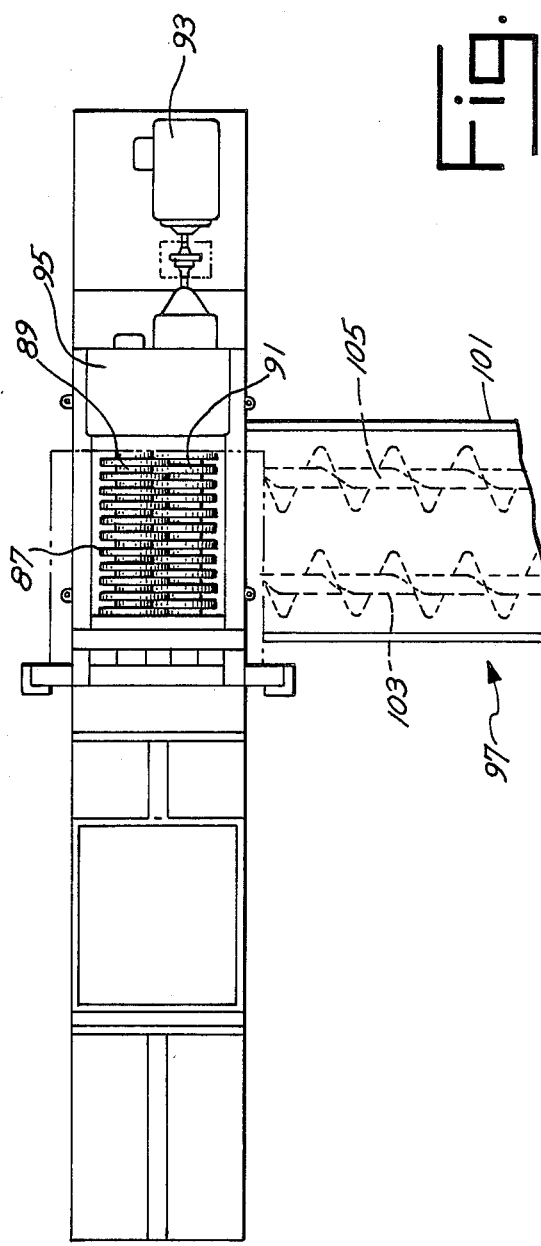
Fig. 3
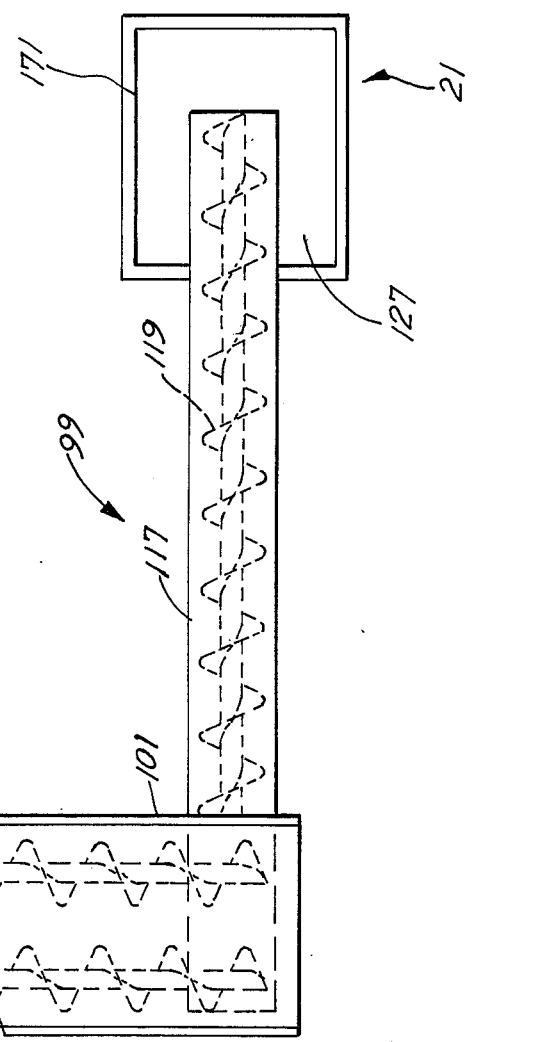
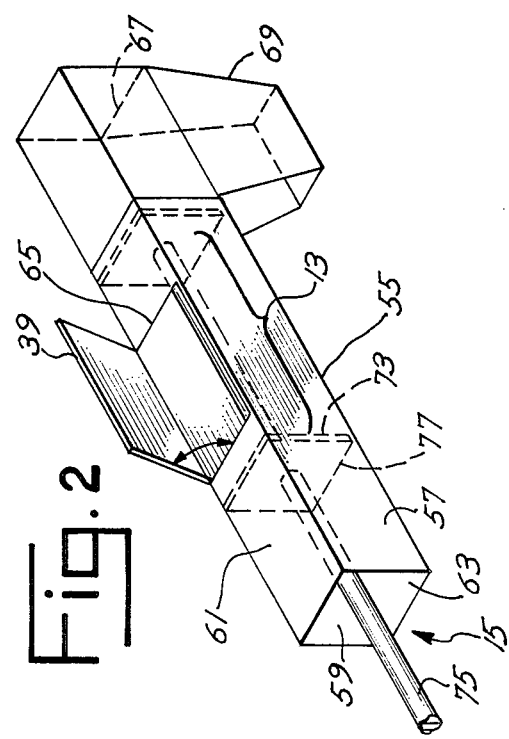
Fig. 2

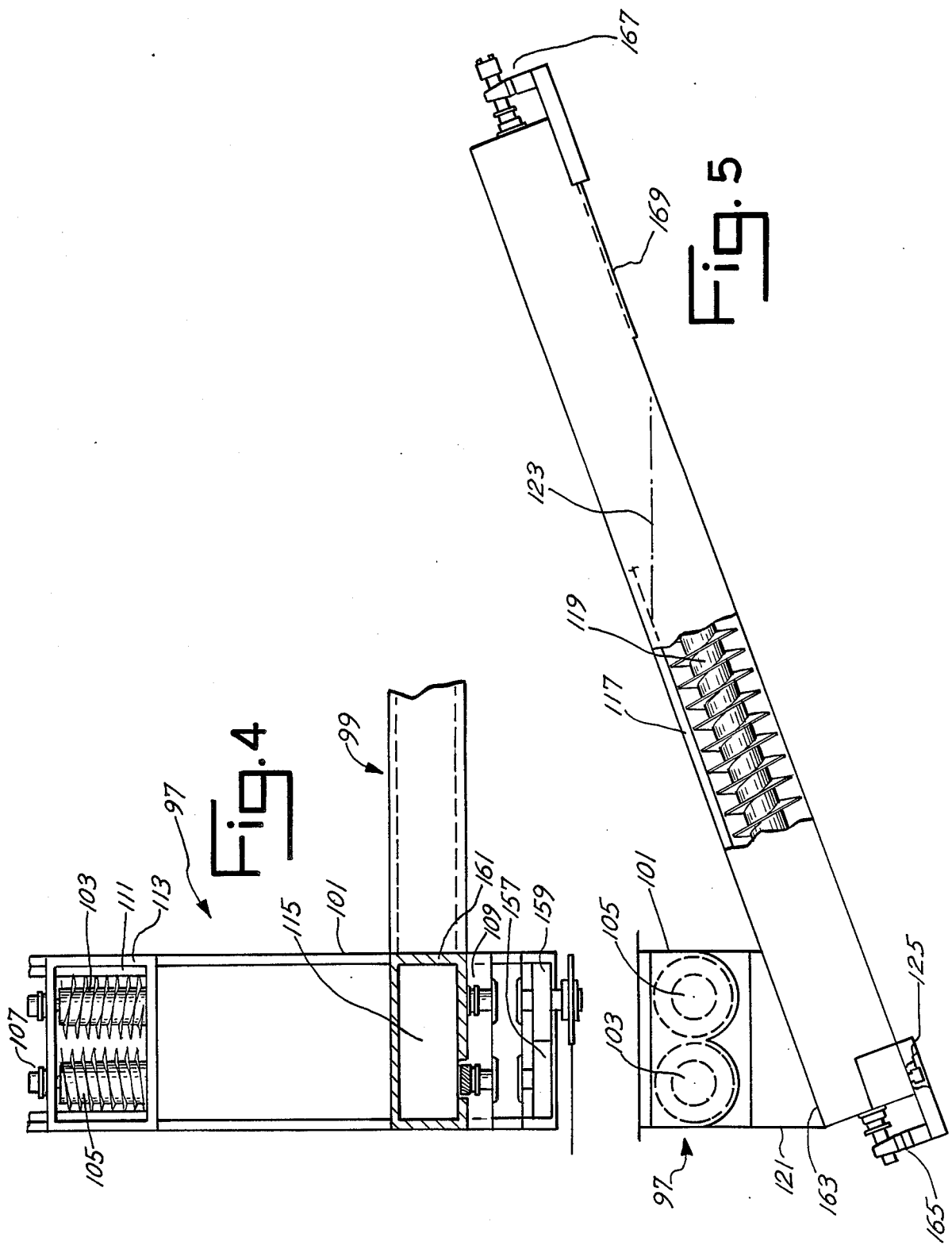

WASTE TREATMENT SYSTEM

BACKGROUND OF THE INVENTION

The invention relates to apparatus for treatment of contaminated waste, and more particularly relates to apparatus for treating medical waste with disinfectant to destroy bacteria and the like.

Land area for the disposal of waste material has become exceedingly scarce, and hazardous waste handling laws have become more stringent. Incineration systems for treating contaminated waste generate unwanted air pollutants while the overall decontamination effectiveness of the costly autoclaving process is questionable. An effective, efficient, and environmentally benign means to decontaminate infectious solid waste is therefore needed. This is particularly true of medical waste which is contaminated with bacteria and the like.

Heretofore, waste treatment systems employing chemical disinfectants direct particulate waste and disinfecting solution into a containing tank where the disinfectant works to decontaminate the waste. Waste particulate settles to the bottom of the containing tank gradually accumulating over a period of time. Eventually the waste particulate is manually removed from the tank by the operator. An example of such a system is disclosed in U.S. Pat. No. 4,619,409.

The extent to which the removal of decontaminated particulate waste is performed by human intervention is related to the safety of the operator controlling and managing the system.

It is therefore an object of the present invention to provide an improved waste treatment system which decontaminates waste.

It is therefore an object of the present invention to provide a waste treatment system which retains and continually agitates waste in disinfecting solution for a pre-determined amount of decontamination time in an environmentally benign manner.

It is a further object of the present invention to provide a waste treatment system which continuously separates waste from disinfectant thereby eliminating the need for dredging a containing tank.

SUMMARY OF THE INVENTION

These and other objects of the present invention are achieved in a waste treatment system which processes infectious solid material. A multi-stage structure facilitates the movement of solid waste through the entire system. The waste enters through a receiving area and is shredded into small pieces of particulate matter by means of a series of disintegrators. Following the shredding process, an enclosed decontamination stage simultaneously retains the waste in disinfecting fluid for a predetermined amount of time, agitates the waste by means of continual movement, and separates the waste from the disinfecting fluid. Finally, the particulate waste is deposited into a discharge bin.

BRIEF DESCRIPTION OF THE DRAWINGS

FIG. 1 is a side view of a waste treatment system embodiment of the invention.

FIG. 2 is a perspective view of a portion of the system of FIG. 1.

FIG. 3 is a top view of the system of FIG. 1.

FIG. 4 is a partial top view of the separating portion of the system of FIG. 1.

FIG. 5 is a side view of the separating portion of FIG. 4.

DETAILED DESCRIPTION OF A PREFERRED EMBODIMENT

Referring to FIG. 1, a waste treatment system 11 includes a receiving bin area 13, a feeding ram 15, a solid waste disintegrator 17, a decontaminator 19, and a discharge bin 21. Contaminated waste enters bin 13 in batches, and is forced by ram 15 into the disintegrator. Disintegrator 17 is formed from three stages of shredders 23,25,27 which serve to successively cut the waste into smaller pieces as the waste moves through the disintegrator.

A plurality of disinfectant spray heads or nozzles 29,31,33,35 are positioned along the path of disintegration and coat the waste pieces in disinfectant as the pieces move through the disintegrator. The disinfectant as well as the waste pieces fall into decontaminator 19 under the force of gravity.

Decontaminator 19 includes an auger network generally indicated by reference numeral 37, which decontaminates and moves the waste pieces from the disintegrator to discharge bin 21. The auger network carries the pieces upwardly with respect to horizontal in order to separate the waste from the disinfectant by gravity prior to the waste entering discharge bin 21.

Referring to FIG. 2, a batch of waste (not shown) enters receiving bin area 13 through a manually operable door 39. Bin area 13 is formed from a portion of a channel 55, a flat rectangular shaped blade 73 and door 39. Channel 55 is formed from two elongated rectangular side members 57,59, a top member 61, and a bottom member 63. Top member 61 includes a rectangular opening 65 the perimeter area of which comes into sealing contact with the outer perimeter area of door 39. Door 39 is rectangular in shape and disposed horizontally when closed. A mechanical or hydraulic control (not shown) serves to open and close door 39 in response to operator control. An operator opens door 39 and manually lifts, shovels, or directs through a conveyor or feed system (not shown) a batch of waste into bin area 13.

Bottom member 63 of the channel 55 includes an opening 67 10 formed at one end of channel 55 which is disposed above disintegrator 17. An infeed hopper 69 depends from opening 67 for funneling waste into disintegrator 17. As shown in FIG. 1, ram channel 55 is inclined at an angle with respect to horizontal for directing loose waste and liquid toward infeed hopper 69.

Referring again to FIG. 2, ram 15 operates within channel 55 for moving waste in bin area 13 towards the end of channel 55 at which point the waste gravitationally falls into infeed hopper 69 through opening 67. Ram 15 includes blade 73 which is driven by a ram rod 75 along channel 55. Rod 75 may be driven by hydraulic controls or other apparatus (not shown).

Initially, blade 73 rests in a first position at 77 to define bin area 13. Door 39 is opened and waste is then fed into the bin area. Door 39 is next closed and then ram blade 73 is forced along channel 55 driving the waste into infeed hopper 69.

Referring again to FIG. 1, negative pressure is applied at point 155 by suitable means (not shown). Acting as a safety mechanism, the negative pressure ensures that airborne bacteria does not feed back into the receiving bin area 13.

As will suggest itself, ram channel 55 may not be used, if desired. Instead, door 39 may be connected directly to the top of infeed hopper 69.

As shown in FIG. 1, shredders 23, 25, and 27 are vertically disposed in tandem for successively reducing the waste into smaller pieces. A plurality of guide channels 81,83,85 depend from respective shredders 23,25,27 for guiding the waste as it exits its respective shredder. Each of guide channels 81 and 83 are connected to the shredder directly above and below in sealing engagement to prevent any bacteria from leaving the disintegrator 17. In like manner, infeed hopper 69 is sealingly connected to the top of shredder 23 and guide channel 85 is sealingly connected to the bottom of shredder 27.

As shown in FIG. 3, each shredder includes a plurality of intermeshing blades 87 for cutting waste into smaller pieces. Blades 87 are arranged on a pair of axles 89,91 which are driven by an electric motor 93 via gear box 95.

In the particular embodiment shown, decontaminator 19 is formed from a pair of decontamination auger conveyors 97 and 99. Conveyor 97 extends horizontally from beneath guide channel 85; whereas conveyor 99 extends from beneath the extended end of the conveyor 97 and slopes upwardly at an approximate angle of 20° to a point disposed above conveyor 97.

As shown in FIG. 4, conveyor 97 includes a rectangular shaped conduit containing a pair of augers 103,105. A rectangular opening 101 in the top of conduit 101 is disposed in alignment with the bottom of guide channel 85 (FIG. 1) for receiving waste therefrom. Channel 85 is connected in sealing engagement with conduit 101 along area 113 surrounding opening 111 for preventing bacteria from seeping into the environment surrounding the waste treatment system. Augers 103 and 105 each having a 25 inch diameter are mounted in sealed bearing members 107,109 at each end of conduit 101 and turn with rotational velocity controlled by timing gears 157 and 159. Timing gears 157 and 159 are driven by a motor or other apparatus (not shown).

Disinfectant fluid is contained within conduit 101 so as to cover augers 103,105 in their entirety. Particulate waste entering conduit 101 by way of opening 111 at the shredder end is slowly and continually moved through the disinfecting fluid by augers 103,105. An opening 115 is formed in the bottom of the extended end of conduit 101 for transferring waste into conveyor 99.

Referring to FIG. 5, conveyor 99 is formed from a shroud or tube 117 and an auger 119. Auger 119 which has 16 inch diameter and is mounted in sealed bearing members 165,167 at each end of tube 117 and is rotated by a motor or other apparatus (not shown).

An opening in the top of tube 117 is disposed in alignment with opening 115 (FIG. 4) in conduit 101. The waste and disinfecting fluid leaving augers 103 and 105 are fed through opening 115 to the receiving end of the auger tube 117 by means of a connecting conduit member 121 located below the output end of the auger conduit 101. The connecting conduit 121 is sealingly connected to both the bottom of conduit 101 along area 161 (FIG. 4). surrounding opening 115 and to the top of tube 117 at location 163.

Particulate waste entering at location 163 in the auger tube 117 is moved through disinfecting fluid by auger 119. Disinfecting fluid is contained within tube 117 to a level 123 covering the portion of auger 119 disposed below level 123.

The duration of time that the waste is retained in the disinfecting fluid contained within conduit 101 and tube 117 is determined by the rate at which augers 103,105 (FIG. 4) and auger 119 (FIG. 5) rotate thereby moving particulate waste through the decontamination phase of the overall system. Rotating at a velocity of 1 RPM, augers 103,105, and 119 must comprise an overall length which ensures that the contaminated waste will be exposed to the disinfecting fluid for a minimum of 120 minutes as called for in current waste treatment requirements. The rotation of augers 103,105, and 119 serves to constantly agitate and mix the waste and disinfecting fluid. Auger 119 continually separates particulate waste from the disinfecting fluid at level 123. The particulate waste emerging from fluid level 123 is free of harmful bacteria and leaves the auger 119 by way of opening 169 located on bottom side of the raised end of auger tube 117. Structure other than augers can be used in the decontamination process in order to retain, agitate, and separate the decontaminated waste in the manner described above.

A bleed off valve 125 is located at the bottom end of tube 117 for providing a bleed off of stale disinfecting fluid. The valve 125 also permits the removal of suspended solids which escape the grasp of the augers in the disinfecting fluid.

Referring again to FIG. 1, a downwardly aimed discharge hood 127 is sealingly attached to auger tube 117 at opening 169. Hood 127 guides decontaminated particulate waste through an opening 171 (FIG. 3) located on top of discharge bin 21.

Discharge bin 21 consists of a cubic structure for receiving decontaminated waste. Periodically, the accumulation of decontaminated waste in discharge bin 21 will require shipment and disposal by conventional means.

What is claimed is:

1. A contaminated waste treatment system for treating contaminated waste, comprising:
    batch input means for receiving the contaminated waste;
    disintegrator means connected to said input means and for reducing the contaminated waste into small pieces;
    decontamination means including: (1) mixing means disposed in a position to receive contaminated waste from said disintegrator means and rotatable for transferring said waste to a discharge position; (2) a conduit surrounding said mixing means; and (3) a disinfectant fluid housed in said conduit and surrounding a portion of said mixing means, said mixing means transferring the contaminated waste through said fluid at a predetermined rate for decontaminating the waste.

2. A contaminated waste treatment system according to claim 1 wherein said mixing means includes auger means for retaining and agitating the waste in said fluid and for transferring the waste through said fluid at a predetermined rate.

3. A contaminated waste treatment system according to claim 2 wherein said auger means is canted with respect to the horizontal, said auger means having a first receiving end disposed beneath said disintegrator means and having a second end disposed vertically higher than said first end, said second end being disposed in said discharge position for transferring said contaminated waste into a discharge bin.

4. A contaminated waste treatment system according to claim 2 wherein said disinfectant fluid is contained within a portion of said auger means.

5. A contaminated waste treatment system according to claim 1 and further including:
   a discharge bin disposed in said discharge position for receiving decontaminated waste from said auger means.

6. A contaminated waste treatment system according to claim 1 wherein said input means includes bin means defining a receiving bin area for receiving contaminated waste, said bin means having a manually operable door.

7. A contaminated waste treatment system according to claim 6 wherein said receiving means further includes a ram means operable for moving said contaminated waste into said disintegrator means.

8. A contaminated waste treatment system according to claim 7 wherein said ram means includes a blade forming one wall of said bin means.

9. A contaminated waste treatment system according to claim 8 wherein said ram means includes a channel means and a ram moveable within said channel means, said channel means includes a lower opening aligned with said input opening of said disintegrator means.

10. A contaminated waste treatment system according to claim 1 wherein said disintegrator means includes shredder means disposed with respect to said receiving means for receiving said contaminated waste and reducing said waste into smaller pieces.

11. A contaminated waste treatment system according to claim 1 wherein said mixing means includes a first area disposed beneath said disintergrator means for receiving said contaminated waste and having a second area extending from said first area for transferring said received contaminated waste to a discharged bin.

* * * * *